United States Patent
Haddock et al.

(10) Patent No.: US 6,884,919 B2
(45) Date of Patent: Apr. 26, 2005

(54) HYDROPHOBIC POLYURETHANE FOAM AS BACKING MATERIAL FOR BANDAGES

(75) Inventors: Teresa Haddock, Hudson, OH (US); Anne Wibaux, Fontainebleau (FR)

(73) Assignee: Johnson & Johnson Consumer Companies, Inc., Skillman, NJ (US)

( * ) Notice: Subject to any disclaimer, the term of this patent is extended or adjusted under 35 U.S.C. 154(b) by 59 days.

(21) Appl. No.: 10/179,674

(22) Filed: Jun. 25, 2002

(65) Prior Publication Data

US 2003/0236478 A1 Dec. 25, 2003

(51) Int. Cl.$^7$ .................................................. A61F 13/00
(52) U.S. Cl. ........................... 602/48; 602/43; 602/54
(58) Field of Search ................................ 602/41–43, 46, 602/54, 56, 30, 22; 2/21; 128/888, 889, 893, 894

(56) References Cited

U.S. PATENT DOCUMENTS 3,645,835 A    2/1972  Hodgson
3,772,224 A  * 11/1973  Marlin et al. ................. 521/124
4,266,043 A  *  5/1981  Fujii et al. .................... 521/175
4,622,089 A  * 11/1986  Lauritzen ..................... 156/250
4,846,164 A     7/1989  Martz
5,947,917 A  *  9/1999  Carte et al. .................... 602/52
2002/0062097 A1 * 5/2002  Simpson ....................... 602/46

FOREIGN PATENT DOCUMENTS

| DE | 4405900 A1 | 12/2000 |
| EP | 0 457 977 A1 | 11/1991 |
| GB | 1 309 768 | 3/1973 |
| JP | 03023860 A | 1/1991 |
| JP | 05285208 A | 11/1993 |

OTHER PUBLICATIONS

European Search Report, 03253965.2–2107–, Oct. 27, 2003.

* cited by examiner

Primary Examiner—Kim M. Lewis

(57) ABSTRACT

The use of hydrophobic polyurethane foam as a backing material for bandages and bandages made with hydrophobic polyurethane foam backings are described. The hydrophobic polyurethane foam has a thickness of from about 0.1 mm to about 0.7 mm. The bandages are flexible, waterproof, and breathable.

9 Claims, No Drawings

HYDROPHOBIC POLYURETHANE FOAM AS BACKING MATERIAL FOR BANDAGES

BACKGROUND OF THE INVENTION

This patent relates to the use of hydrophobic polyurethane foam as a backing material for bandages and to bandages made with a hydrophobic polyurethane foam backing. The hydrophobic polyurethane foam is relatively thick. The hydrophobic polyurethane foam permits water vapor to escape from the surface of the skin, but keeps liquid water from reaching the surface of the skin.

It is well known to apply adhesive bandages (also known as wound dressings) to wounds to protect the wound and keep the wound clean. Most commonly, the bandages are made from a polyethylene or polyvinyl chloride backing material. One side of the backing material generally contains a centralized pad, which is utilized to keep the wound clean and to cushion the wound. Adhesives are used alongside the pad to hold the bandage in place. The polyethylene backing material does not allow water vapor to leave the surface of the skin covered by the bandage. This leads to discomfort for the user. In order to overcome this problem, bandages generally are apertured, that is, the polyethylene film is perforated to allow water vapor to leave the surface of the skin.

Although apertured films are useful, there is a concern that the apertures allow liquid water to reach the surface of the skin and the wound. The presence of water promotes bacterial growth, which can lead to an infection of the wound. Therefore, there is a need for a bandage that allows water vapor to evaporate from the surface of the skin under the bandage (is "breathable"), but does not let liquid water reach the surface of the skin under the bandage (is "waterproof").

The use of thin breathable films, such as 0.025 mm polyurethane as the backing material for a wound dressing has been practiced since the 1970s. U.S. Pat. No. 3,645,835 disclosed this type of adhesive dressing for blocking bacteria and liquid water from reaching the wound, but allowing oxygen to penetrate the dressing from the atmosphere and allowing moisture from the skin of the patent to escape from beneath the dressing.

The moisture vapor transmission rate ("MVTR") measures the degree of breathability of a film. In order to obtain the desired MVTR, these types of films are generally thin, ie. less than 0.05 mm in thickness. Because of the nature of polymers used for breathable films, breathable films made at the thickness of 0.05 mm or less are generally flexible, limp, flimsy and hard to handle. When adhesive is applied on the film to enable the film dressing to adhere to the skin, the film tends to stick to itself wherever adhesive surfaces touch each other. This makes it difficult to apply the thin breathable film dressings to the skin.

To overcome this problem, delivery systems have been designed to handle these types of dressings. U.S. Pat. Nos. 4,413,621 and 4,485,809 are two examples. One disadvantage of thin breathable film dressings with delivery systems is that it is sometimes difficult for users to figure out how to use them. Another disadvantage of thin breathable film dressings with delivery systems is that it is sometimes difficult for users to use the delivery system.

Another method to improve the ability to handle thin breathable films was taught in U.S. Pat. No. 4,846,164. The patent taught the use of composites, which combined thin films with other materials. U.S. Pat. No. 4,773,409 also taught the use of composites for bandages. The composites included a polyurethane film and a polyurethane foam containing water dispersible or water swellable agents. Composite bandages are generally more expensive to produce than the thin film. Additionally, the presence of water swellable agents might not be desirable, as the result would be a moist surface against the wound, which would promote bacterial growth, and possibly an infection of the wound.

Therefore, despite the disclosure of the references, there is a continuing need for a bandage that is breathable, but is waterproof, and is easy to handle and apply to a wound.

SUMMARY OF THE INVENTION

The present invention provides a bandage including: a hydrophobic polyurethane foam backing; and a pad configured as an island pad; wherein the polyurethane foam has a thickness of from about 0.1 mm to about 0.7 mm.

DETAILED DESCRIPTION OF THE INVENTION

The bandage of the present invention is conformable, breathable and waterproof. The backing material may be made of any hydrophobic polyurethane foam. Hydrophobic polyurethane foams are well known in the art and are generally made by reacting polyisocyanates with polyols. One example, although not limiting, of suitable hydrophobic polyurethane foams and a process for their preparation is described in U.S. Pat. No. 3,772,224, hereby incorporated by reference. Such hydrophobic polyurethane foams are commercially available, for example, as PORON® polyurethane foams available through Rogers Company, and TIELLE® polyurethane foams available through Mediflex Company. The hydrophobic polyurethane foam may have a thickness ranging from about 0.1 mm to about 0.7 mm, preferably from about 0.2 mm to about 0.5 mm, more preferably from about 0.25 mm to about 0.4 mm.

The hydrophobic polyurethane foam contains cells, which are bubbles that were created when gas was evolved during the process of making the polyurethane. The size of the cells may range from about 0.0001 $mm^2$ to about 0.050 $mm^2$. The overall average cell size may range from about 0.001 $mm^2$ to about 0.010 $mm^2$, preferably from about 0.002 $mm^2$ to about 0.008 $mm^2$. The hydrophobic polyurethane foam may be open-celled or closed-celled, but preferably is closed-cell. As used herein, closed-cell means the surface of the foam away from the skin or wound is sealed either thermally or through the use of a coating.

The pad is designed to keep the wound clean and dry, absorb exudate from the wound, and to provide cushioning for the wound. Therefore, the pad must be in an island pad configuration. Both the polyurethane foam backing and the pad have horizontal edges. As used herein, island pad configuration means that the horizontal edges of the pad do not reach the horizontal edges of the polyurethane foam backing.

The pad may be made from any absorbent material. Suitable absorbent materials may be made from various materials including gels, hydrocolloids, alginates, Rayon, natural fibers, such as, but not limited to, cotton and wood pulp, synthetic fibers, such as, but not limited to, polyester, polyamide, and polyolefin, copolymers thereof, and combinations thereof. The fibers may be bicomponent fibers. For example, the fibers may have a core of one polymer, and a sheath of a different polymer.

The pad may be bonded. As used herein, bonded means that the pad is made of fibers, which cross over, and are in contact with each other. The fibers are either heated, or an adhesive is added to the fibers until the fibers fuse with neighboring fibers where they intersect and contact each other. Hollow fibers and straight extruded fibers of diameter from 3 to 10 denier can be bonded. A partcularly useful bonded pad material is PGI's ENKA fiber.

The pad may have a top sheet, which is useful to prevent the wound from sticking to the pad. Suitable materials for the top sheet include, but are not limited to polyolefins, such as polyethylene, and polyvinyl acetate.

The adhesive used on the bandage can be any adhesive, including pressure sensitive adhesive such as acrylic based, rubber based, silicone based, and polyurethane based adhesives. Examples of suitable adhesives include, but are not limited to, AS968LV (acrylic based adhesive available through Avery Dennison), GMS2999 (acrylic based adhesive available through Solutia), GE6574 (diphenyl siloxane rubber based adhesive available through General Electric) and GE595 (dimethyl siloxane rubber based adhesive available through General Electric).

The adhesive may be applied to the entire surface of the polyurethane foam backing which faces the wound ("continuous"), or may be applied in a discontinuous fashion, such as by spray coating. When the adhesive is applied as a discontinuous coating, the adhesive should cover about 70 percent and above of the wound facing surface of the polyurethane foam backing, preferably about 85 percent and above of the wound facing surface of the polyurethane foam backing.

The adhesive provides a strong bond between the bandage and the skin. As is common practice, the adhesive surface may be protected by a piece of release paper prior to applying the bandage to the skin. Suitable release papers are well known in the art.

The bandage has a MVTR above 500 $g/m^2/24$ hrs, preferably above 1,000 $g/m^2/24hrs$. Since the bandage is breathable, there is no need for perforation as commonly used on adhesive bandages. The bandage has a bulk thickness of at least about 0.035 mm.

Bandages are typically tested on an Instron testing machine. The bandages of this invention have an immediate recovery of at least about 70% and an energy recovery of at least about 50% when stretched up to 20% of the original length of the bandage. The bandages have an immediate recovery of at least about 75% and an energy recovery of at least about 40% when stretched up to 50% of the original length of the bandage. Most preferably, the immediate recovery is over about 90%; with this property, the bandage will conform according to body movement when used on joints such as the knuckles.

Stretch and Recovery Test

The first step in the stretch and recovery test was to condition the samples at 50% relative humidity and 75° F. for at least 4 hours. An Instron testing machine was utilized with a pulling clamp speed of 12.5 cm per minute. The machine had a cycling control that was adjustable to allow the stressing of the sample to a certain distance and returning immediately to the gage length at the same speed. The faces on the jaws of the machine measured at least 2.5 cm×3.75 cm, with the long dimension perpendicular to the direction of application of the load. The distance between the clamps was 10 cm at the start of the test. The jaws had smooth gripping surfaces.

The samples were clamped firmly and squarely in the jaws of the clamps. The cycle extension limits were set to reflect the amount of extension required (5% extension required 0.13 cm×10 cm gage length=0.5 cm maximum limit on the cycle control). Force was applied to the samples at a rate of 12.5 cm per minute, such that the sample was stressed to the desired length of extension, and returned at the same speed from that point. The immediate recovery was the distance for the sample to reach the baseline from maximum force, divided by the distance for the sample to reach maximum force from initiation of the test, times 100.

Water Leakage Test

To determine whether this type of construction provides a waterproof bandage, a laboratory water leakage test was developed to test the product. Bandages were adhered to a clean 6.2 cm×20 cm glass plate. The bandages were rolled or pressed to remove any air bubbles and ensure removal of any voids in the adhesive/glass interface. The sample sat for 5 minutes. The glass plates with the bandages were placed upside-down in a 30 cm×45 cm, 3.7 cm to 5 cm deep glass tray or dish. A red dye solution (0.1% red dye in water) was poured into the dish so that the dye just reached the level of the glass plates, but did not cover them. A stop watch was started and the time for the dye to penetrate the adhesive-seal was determined (as indicated visually when the dye reached the pad). The test was run for five replicates of each sample. Bandages are considered waterproof if the time for the dye to reach the pad exceeds 30 minutes. Therefore, hydrophobic polyurethanes are those that do not let dyed water penetrate to the pad for at least 30 minutes.

Moisture Vapor Transmission Rate

The MVTR was measured following ASTM method F1249. The MVTR was considered acceptable if it was greater than 500 $g/m^2/24hrs$.

EXAMPLES

Bandages were prepared using a 2 cm×7 cm, 0.33 mm thick PORON polyurethane foam as the backing material. AS968 adhesive (lot I-663) was applied at 35 grams per square meter on the backing by transfer coating. The adhesive was spread on a release-coated paper and contacted with the backing material under sufficient pressure to ensure good adhesive anchorage on the backing. The release liner was then removed. A 2.2 cm×1.2 cm AET (3.7 ounce, 90/10 polyester/rayon) pad was placed on each backing. This construction was then covered with the facing tab (release liner) and cut to a bandage in such a way that the pad was centrally placed on the bandage.

The bandages were tested as described above for stretch and recovery, water leakage, and MVTR. The results are shown in Tables 1, 2, and 3.

TABLE 1

|        | 20% Stretch and Recovery | | 50% Stretch and Recovery | |
|--------|---------------|------------|---------------|------------|
| Sample | Immediate (%) | Energy (%) | Immediate (%) | Energy (%) |
| 1      | 96.6          | 58.9       | 90.6          | 43.8       |
| 2      | 96.6          | 54.1       | 91.4          | 46.3       |

Both samples passed the immediate recovery and energy recovery tests, and are therefore useful for waterproof bandages on areas of the body that flex, such as the fingers and elbows.

TABLE 2

| Sample | Time To Penetrate (minutes) |
|---|---|
| 1 | >60 |
| 2 | >60 |

Both samples resisted penetration of the dyed water to the pad for greater than 60 minutes, therefore, the samples are useful for waterproof bandages.

TABLE 3

| Sample | MVTR (g/m$^2$/24 hrs) |
|---|---|
| 1 | 1250 |
| 2 | 1203 |

Both samples had a MVTR greater than 500 g/m$^2$/24 hrs, therefore the samples are breathable. The data above demonstrates that the bandages of the invention are flexible, breathable, and waterproof.

We claim:

1. A bandage comprising:
    a hydrophobic polyurethane foam backing; and
    an island pad;
    wherein the polyurethane foam backing has a thickness of from about 0.1 mm to about 0.7 mm and the bandage has an immediate recovery of at least 70% and an energy recovery of at least 50% when stretched up to 20% of the original length of the bandage.

2. The bandage of claim 1, wherein the hydrophobic polyurethane foam backing is selected from those prepared by the reaction of a polyisocyanate with a polyol.

3. The bandage of claim 1, wherein the polyurethane foam backing has a thickness of from about 0.2 mm to about 0.5 mm.

4. The bandage of claim 1, wherein the polyurethane foam backing has a thickness of from about 0.25 mm to about 0.4 mm.

5. The bandage of claim 1, wherein the bandage has an immediate recovery of at least 75% and an energy recovery of at least 40% when stretched up to 50% of the original length of the bandage.

6. The bandage of claim 1, wherein the bandage has an immediate recovery of over 90% when stretched up to 20% of the original length of the bandage.

7. The bandage of claim 1, wherein the bandage has an immediate recovery of over 90% when stretched up to 50% of the original length of the bandage.

8. The bandage of claim 1, wherein the bandage has a moisture vapor transmission rate of above 500 g/m$^2$/24 hrs.

9. The bandage of claim 1, wherein the bandage has a moisture vapor transmission rate of above 1000 g/m$^2$/24 hrs.

* * * * *